United States Patent
Sampson

(10) Patent No.: US 6,424,137 B1
(45) Date of Patent: Jul. 23, 2002

(54) USE OF ACOUSTIC SPECTRAL ANALYSIS FOR MONITORING/CONTROL OF CMP PROCESSES

(75) Inventor: Ronald Kevin Sampson, Fountain Hills, AZ (US)

(73) Assignee: STMicroelectronics, Inc., Carrollton, TX (US)

( * ) Notice: Subject to any disclaimer, the term of this patent is extended or adjusted under 35 U.S.C. 154(b) by 82 days.

(21) Appl. No.: 09/663,646

(22) Filed: Sep. 18, 2000

(51) Int. Cl.[7] .............................................. G01R 23/16
(52) U.S. Cl. ................... 324/76.21; 324/76.22; 451/5
(58) Field of Search .......................... 324/76.19, 76.21, 324/76.22; 340/680; 451/5, 8, 41

(56) References Cited

U.S. PATENT DOCUMENTS

| | | | |
|---|---|---|---|
| 5,209,816 A | 5/1993 | Yu et al. ........................ 156/636 |
| 5,222,329 A | 6/1993 | Yu ............................ 51/165.77 |
| 5,240,552 A | 8/1993 | Yu et al. ........................ 156/636 |
| 5,245,794 A | 9/1993 | Salugsugan ................ 51/165.74 |
| 5,399,234 A | 3/1995 | Yu et al. ....................... 156/636 |
| 5,439,551 A | 8/1995 | Meikle et al. ............ 156/626.1 |
| 5,469,742 A | 11/1995 | Lee et al. ....................... 73/597 |
| 5,575,706 A | 11/1996 | Tsai et al. ....................... 451/41 |
| 5,700,180 A | * 12/1997 | Sandhu et al. ................. 451/21 |
| 5,705,435 A | 1/1998 | Chen .............................. 438/8 |
| 5,996,415 A | 12/1999 | Stanke et al. ................... 73/597 |
| 6,008,119 A | 12/1999 | Fournier ....................... 438/633 |

* cited by examiner

Primary Examiner—Michael J. Sherry
Assistant Examiner—Tung Nguyen
(74) Attorney, Agent, or Firm—Lisa K. Jorgenson; Daniel E. Venglarik

(57) ABSTRACT

Acoustic emission samples for a chemical mechanical polishing process are acquired and analyzed using a Fourier transform to detect wafer vibrations characteristic of scratching. When excess noise levels are detected at frequencies or within frequency bands being monitored, the polishing process is halted and an alarm is generated for the operator. Such in-situ detection minimizes damage to the wafer being polished and limits the damage to a single wafer rather than a run of wafers. Polish endpoint detection may be integrated within the scratch detection mechanism.

20 Claims, 2 Drawing Sheets

USE OF ACOUSTIC SPECTRAL ANALYSIS FOR MONITORING/CONTROL OF CMP PROCESSES

BACKGROUND OF THE INVENTION

1. Field of the Invention

The present invention relates to chemical mechanical polishing processes and in particular to detecting scratching of substrates during chemical mechanical polishing. Still more particularly, the present invention relates to employing acoustic spectral analysis during chemical mechanical polishing to detect abnormal vibrations indicating scratching of a substrate being polished.

2. Description of the Prior Art

Chemical mechanical polishing (CMP) processes are commonly employed in place of wet or dry etching to remove material from a substrate during semiconductor device fabrication. Such chemical mechanical polishing typically involves saturating a polyester polishing pad mounted on a polishing platen with an abrasive, chemical etchant polishing slurry, then lowering a chuck holding a wafer until the wafer surface to be polished contacts the saturated surface of the polishing pad. The polishing platen and pad are then rotated, usually with the chuck and wafer being independently rotated, while the wafer surface and the polishing pad are in contact until a desired amount of material has been removed.

Occasionally a scratch-causing particle—such as a metal fragment broken off from the substrate being polished—will become trapped on or within the polishing pad during chemical mechanical polishing. Since device features may be destroyed or proper feature spacing precluded by scratching, such scratch-causing particles usually ruin the wafer, or at least a significant portion of the integrated circuit die on the wafer.

Current ex-situ control of chemical mechanical polishing processes employ visual inspection and/or optical testing of the polished wafers to detect scratching. Due to batch processing considerations and other factors introducing delay between the chemical mechanical polishing and analysis of the polished wafers for scratching, a large number of wafers may become scratched by a particle embedded within the polishing pad before such scratching is detected. Typically a minimum of 25 wafers—and often as many as 400 wafers or more—may be damaged or destroyed before detection of the problem and replacement of the polishing pad.

It would be desirable, therefore, to provide an in-situ mechanism for detecting scratching of wafers during chemical mechanical polishing.

SUMMARY OF THE INVENTION

Acoustic emission samples for a chemical mechanical polishing process are acquired and analyzed using a Fourier transform to detect wafer vibrations characteristic of scratching. When excess noise levels are detected at frequencies or within frequency bands being monitored, the polishing process is halted and an alarm is generated for the operator. Such in-situ detection minimizes damage to the wafer being polished and limits the damage to a single wafer rather than a run of wafers. Polish endpoint detection may be integrated within the scratch detection mechanism.

BRIEF DESCRIPTION OF THE DRAWINGS

The novel features believed characteristic of the invention are set forth in the appended claims. The invention itself however, as well as a preferred mode of use, and further objects and advantages thereof, will best be understood by reference to the following detailed description of an illustrative embodiment when read in conjunction with the accompanying drawings, wherein:

DETAILED DESCRIPTION

The following description details the structure, application and features of the present invention, but it will be understood by those of skill in the art that the scope of the invention is defined only by the issued claims, and not by any description herein. The process steps and structures described below do not form a complete process flow for manufacturing integrated circuits. The present invention may be practiced in conjunction with common integrated circuit fabrication techniques, and only so much of the commonly practiced process steps are included as are necessary for an understanding of the present invention. The figures are not drawn to scale, but instead are drawn so as to illustrate the important features of the invention.

Figure 1:
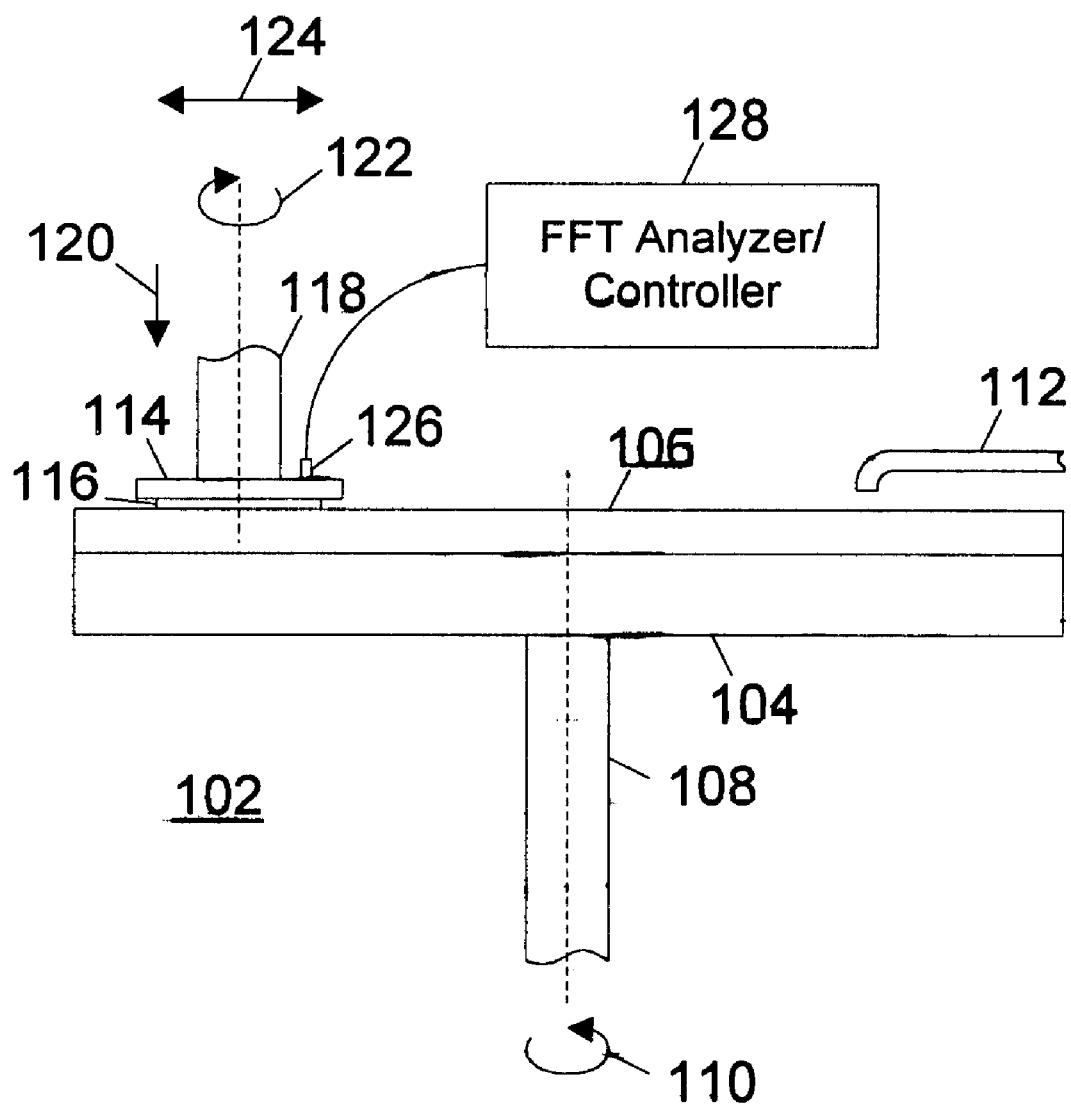
FIG. 1 depicts a pictorial diagram of a chemical mechanical wafer polishing process with in-situ detection of scratch-causing particles in accordance with a preferred embodiment.

With reference now to the figures, and in particular with reference to FIG. 1, a pictorial diagram of a chemical mechanical wafer polishing process with in-situ detection of scratch-causing particles in accordance with a preferred embodiment is depicted. Wafer polisher 102 includes a polishing platen 104 to which the polishing pad 106 is affixed. Polishing platen 104 includes a connection 108 to a drive mechanism (not shown) which enables the platen 104 and pad 106 to be rotated in at least one rotational direction 110. A conduit 112 dispenses a polishing slurry, typically silica or alumina abrasive particles suspended in either a basic or an acidic solution, onto polishing pad 106.

A wafer chuck 114 holds a wafer 116 to be polished, usually by vacuum means. Wafer chuck 114 includes a connection 118 to one or more drive mechanisms (not shown) which enable the wafer chuck 114 to be selectively lowered 120 until wafer 116 contacts polishing pad 106 with a desired amount of force, rotated in at least one rotational direction 122, and moved transversely in a direction 124 which is radial with respect to polishing platen 104.

One or more acoustic transducers 126 are situated proximate to the contact region between wafer 116 and polishing pad 106. In the depicted example, transducer 126 is mounted on wafer chuck 114, although one or more transducers (in addition to other transducers which may be mounted on wafer chuck 114) may also be mounted on polishing platen 104. Each transducer 126 is connected to an analyzer and controller 128, which analyzes the measured acoustic waveforms and controls the drive mechanisms coupled to wafer chuck 114 and polishing platen 104 and driving the mechanical aspect of the polishing process.

The acoustic waveform detected by transducer 126 is sampled over periodic intervals. The sample period and the sampling resolution within each interval are selected to optimize detection of harmonic frequencies indicating the presence of a scratch-inducing particle, as described in further detail below. A Fourier transform, preferably a fast Fourier transform (FFT), is performed on the time-dependent signal within each sample to generate a spectral image of the acoustic noise generated by the polishing process. The spectral content of the detected acoustic signal is then analyzed. Since the polishing process is at least partially mechanical, abnormal conditions such as the presence of a scratch-causing particle between the wafer 116 and the polishing pad 106/platen 104 may be detected by abnormal vibrations (acoustics) resulting from the scratching process.

Examination of the physical scratch defect appearing on a wafer surface as a result of a particle or other impurity becoming embedded within the polishing pad reveals localized damage in the form of a periodic series of indentations. The periodic nature of this damage indicates a vibration during contact of the impurity with the wafer surface. By detecting this vibration, the polishing process may be halted prior to serious damage to the wafer.

Numerous polish endpoint detection mechanisms employing acoustic sensors, generally measuring the level, frequency, or reflection time for acoustic emissions of the polishing process, have been proposed or employed. Such endpoint detection—that is, a shift in the frequency peaks when the polish material changes from oxide to a nitride etch stop layer or from metal or oxide—may be integrated with the analysis and monitoring system of the present invention. However, the presence of a scratch-causing defect will result in the appearance or many harmonics, which renders monitoring of a single frequency (such as for endpoint control purposes) unreliable for scratch detection purposes.

Generally the presence of particles or other impurities embedded into the surface of polishing pad 106, or physically located between polishing pad 106 and wafer 116, will alter the vibration or spectral emissions emanating from the polishing process. Performance of a fast Fourier transform on such emissions allows specific frequencies or frequency bands to be monitored for changes. An output of the Fourier transform in excess of a threshold at specific frequencies or frequency bands will indicate scratching of the wafer.

A reference spectrum established by comparing the emissions of the polishing process without scratch-causing particles and with scratch-causing particles intentionally introduced enables determination of appropriate sampling intervals and the frequencies or frequency bands to monitor to facilitate early detection of anomalies. The characteristic spectral response from defects should be sufficiently noisy to negate the need for a baseline analysis at the beginning of each polishing process.

Figure 2:
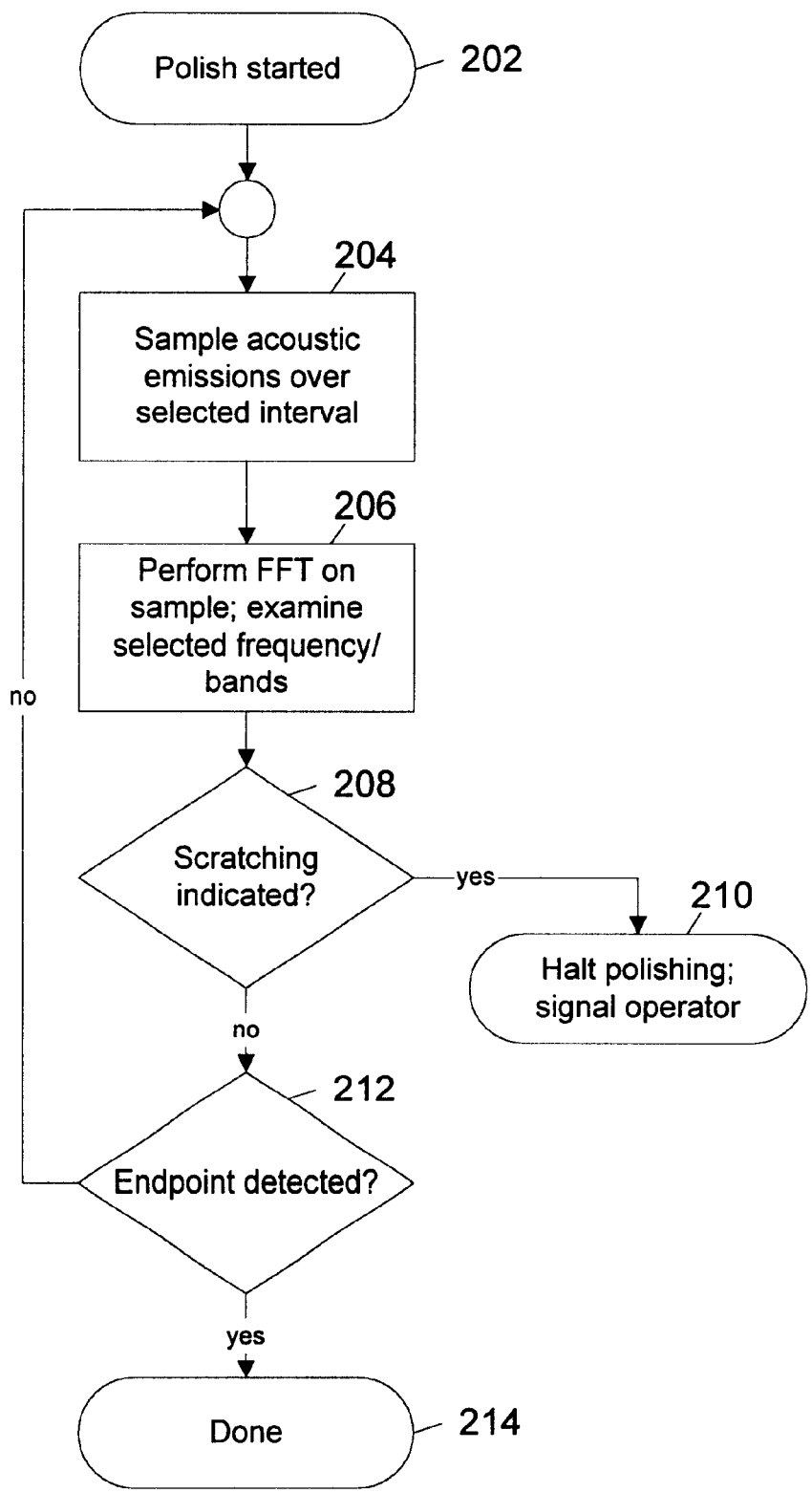
FIG. 2 is a high level flow chart for a process of detecting wafer damage during polishing in accordance with a preferred embodiment of the present invention.

Referring to FIG. 2, a high level flow chart for a process of detecting wafer damage during polishing in accordance with a preferred embodiment of the present invention is illustrated. The process begins at step 202, which depicts chemical-mechanical polishing of a wafer being initiated, such as by loading a wafer from a cassette onto the wafer chuck and lowering the wafer into contact with the polishing pad while one or both of the wafer and the polishing pad are rotated.

The process first passes to step 204, which illustrates sampling acoustic emissions from the polishing process over a selected time interval. The optimal time interval should be selected after analyzing spectral emissions of a polishing process into which scratch-causing particles have been intentionally introduced, but generally should not exceed a few seconds. The process next passes to step 206, which depicts performing a Fourier transform—preferably a fast Fourier transform—on the sampled acoustic emissions to determine noise levels at one or more preselected frequencies or within one or more preselected frequency bands.

Again, the frequencies or frequency bands which should be monitored may be determined from analysis of a polishing process during which scratching occurs. The noise levels at the selected frequencies or within the selected bands are examined for an indication of scratching during the polishing process.

The process passes next to step 208, which illustrates a determination of whether scratching of the wafer is indicated from the analysis of the sample acoustic emissions. If so, the process proceeds to step 210, which illustrates halting the polishing process and signaling an operator, who may then remove the scratched wafer from the chemical-mechanical polisher and clean or replace the polishing pad, as warranted. If no scratching of the wafer being polished is indicated by the sampled acoustic emissions, however, the process proceeds instead to step 212, which indicates a determination of whether the polish endpoint has been reached. Numerous conventional polish endpoint detection schemes may be employed, although frequency-shift based detection may be more readily integrated with the FFT analysis of the present invention.

If the polish endpoint has not yet been reached, the process returns to step 204 to acquire another sample of the acoustic emissions from the polishing process. Those skilled in the art will recognize that, in practice, step 204 is likely to be performed concurrently with steps 206, 208, and 212. That is, a sample of the polishing process' acoustic emissions will be acquired at the same time that one or more previous samples is processed and analyzed for an indication of scratching and/or endpoint detection. Once the polish endpoint has been detected, the process proceeds from step 212 to step 214, which depicts the process becoming idle until polishing of another wafer is initiated (e.g., the next wafer from the cassette is retrieved and mounted for polishing).

The present invention employs detection of lower order harmonics relating to wafer vibration for in-situ detection of scratching during chemical mechanical polishing. Noise acquired by an acoustic transducer proximate to the polishing process is analyzed using a Fourier transform to identify alarming noise levels within the appropriate harmonics. The process may be stopped before serious damage to the wafer being polished occurs. In any event, damage is limited to a single wafer even with batch processing. Since vibration may be localized and somewhat damped over distance, multiple acoustic transducers may be employed for large wafers (e.g., ten inches or larger).

While the invention has been particularly shown and described with reference to a preferred embodiment, it will be understood by those skilled in the art that various changes in form and detail may be made therein without departing from the spirit and scope of the invention.

What is claimed is:

1. A chemical mechanical polisher, comprising:
    a polishing platen on which a polishing pad is selectively mounted;
    a wafer chuck on which a wafer to be polished is mounted, the wafer chuck capable of being selectively lowered until the wafer contacts the polishing pad;
    an acoustic transducer positioned proximate to a contact region between the wafer and the polishing pad;
    an analyzer performing a Fourier transform on samples acquired by the acoustic transducer and examining the output of the Fourier transform for noise indicating scratching of the wafer; and
    a controller halting polishing of the wafer upon detection of noise indicating scratching of the wafer.

2. The chemical mechanical polisher of claim 1, wherein the analyzer performs a fast Fourier transform on samples acquired by the acoustic transducer.

3. The chemical mechanical polisher of claim 1, wherein the acoustic transducer is mounted on the wafer chuck.

4. The chemical mechanical polisher of claim 1, further comprising:

a plurality of acoustic transducers mounted on the wafer chuck.

5. The chemical mechanical polisher of claim 1, wherein the controller generates an alarm for an operator after halting polishing of the wafer.

6. The chemical mechanical polisher of claim 1, wherein the analyzer examines an output of the Fourier transform at a preselected frequency or within a preselected frequency band.

7. The chemical mechanical polisher of claim 6, wherein an output of the Fourier transform in excess of a threshold at a preselected frequency or within a preselected frequency band indicates scratching of the wafer.

8. The chemical mechanical polisher of claim 1, wherein the analyzer examines an output of the Fourier transform for a shift of a fundamental frequency indicating a polish endpoint.

9. A method of detecting wafer damage during polishing, comprising:

polishing a wafer utilizing a chemical mechanical polishing process;

monitoring at least one preselected frequency or preselected frequency band within acoustic emissions of the polishing process for noise indicating scratching of the wafer; and automatically halting the polishing process upon detection, within the at least one preselected frequency or preselected frequency band, of noise indicating scratching of the wafer.

10. The method of claim 9, wherein the step of monitoring at least one preselected frequency or preselected frequency band within acoustic emissions of the polishing process for noise indicating scratching of the wafer further comprises:

sampling the acoustic emissions of the polishing process for a selected time interval;

performing a Fourier transform on the sampled acoustic emissions; and examining an output of the Fourier transform for the at least one preselected frequency or frequency band.

11. The method of claim 10, wherein the step of performing a Fourier transform on the sampled acoustic emissions further comprises:

performing a fast Fourier transform on the sampled acoustic emissions.

12. The method of claim 10, wherein the step of examining an output of the Fourier transform for the at least one preselected frequency or frequency band further comprises:

examining the output of the Fourier transform for a frequency shift identifying a polish endpoint.

13. The method of claim 9, further comprising:

after halting the polishing process upon detection of noise indicating scratching of the wafer, generating an alarm for an operator.

14. The method of claim 9, further comprising:

monitoring the polishing process for a polish endpoint.

15. A mechanism for detecting wafer damage during polishing, comprising:

means for polishing a wafer utilizing a chemical mechanical polishing process;

means for monitoring at least one preselected frequency or preselected frequency band within acoustic emissions of the polishing process for noise indicating scratching of the wafer; and means for automatically halting the polishing process upon detection, within the at least one preselected frequency or preselected frequency band, of noise indicating scratching of the wafer.

16. The mechanism of claim 15, wherein the means for monitoring at least one preselected frequency or preselected frequency band within acoustic emissions of the polishing process for noise indicating scratching of the wafer further comprises:

means for sampling the acoustic emissions of the polishing process for a selected time interval;

means for performing a Fourier transform on the sampled acoustic emissions; and means for examining an output of the Fourier transform for the at least one preselected frequency or frequency band.

17. The mechanism of claim 16, wherein the means for performing a Fourier transform on the sampled acoustic emissions further comprises:

means for performing a fast Fourier transform on the sampled acoustic emissions.

18. The mechanism of claim 16, wherein the means for examining an output of the Fourier transform for the at least one preselected frequency or frequency band further comprises:

means for examining the output of the Fourier transform for a frequency shift identifying a polish endpoint.

19. The mechanism of claim 15, further comprising:

means, after halting the polishing process upon detection of noise indicating scratching of the wafer, for generating an alarm for an operator.

20. The mechanism of claim 15, further comprising:

means for monitoring the polishing process for a polish endpoint.

* * * * *